United States Patent [19]

Tan et al.

[11] Patent Number: 4,485,017

[45] Date of Patent: Nov. 27, 1984

[54] ISOLATION OF HUMAN INTERFERON BY IMMUNOSORBENT AND HIGH PERFORMANCE LIQUID CHROMATOGRAPHY

[75] Inventors: Yin H. Tan; Heidi Smith-Johannsen, both of Calgary, Canada

[73] Assignee: Cetus Corporation, Emeryville, Calif.

[21] Appl. No.: 452,189

[22] Filed: Dec. 22, 1982

[51] Int. Cl.³ .............................................. B01B 15/08
[52] U.S. Cl. .................................... 210/635; 210/656; 260/112.5 R; 435/811
[58] Field of Search .................. 210/635, 656, 644; 435/811; 260/112.5 R; 424/85

[56] References Cited

U.S. PATENT DOCUMENTS

| 4,125,492 | 11/1978 | Cuatrecasas | 210/656 |
| 4,257,938 | 3/1981 | Hosoi | 210/656 |
| 4,283,199 | 8/1981 | Szabo | 210/656 |
| 4,289,189 | 9/1981 | Pestra et al. | 260/112 R |
| 4,350,760 | 9/1982 | Nicolas et al. | 210/635 |
| 4,359,389 | 11/1982 | Heine | 210/656 |

OTHER PUBLICATIONS

Introduction to Modern Liquid Chromatography by Snyder et al., 2nd edition, John Wiley & Sons of N.Y., pp. 285-289, 454 and 455, 1979.

Primary Examiner—John Adee
Attorney, Agent, or Firm—Albert P. Halluin; Shyamala T. Rajender; Kate H. Murashige

[57] ABSTRACT

An improved process for the isolation and purification of HIFNs is disclosed wherein a partially purified preparation of the HIFN is sequentially passed through an antibody affinity column and a reversed-phase high performance liquid chromatographic column. Organic solvents used during the elution are extracted and the protein concentrated for subsequent use.

12 Claims, 3 Drawing Figures

ISOLATION OF HUMAN INTERFERON BY IMMUNOSORBENT AND HIGH PERFORMANCE LIQUID CHROMATOGRAPHY

This invention is in the field of biochemistry and more specifically, in the area of protein chemistry. Still more specifically, the invention relates to a process for the biochemical isolation and purification of human interferons.

Since their discovery in 1957, interferons have been extensively and intensively investigated for their potential therapeutic use as antiviral and anti-proliferative agents. Interferons (IFNs) are species-specific glycoproteins produced by various cells upon induction with viruses, double stranded RNAs, other polynucleotides, antigens and mitogens. Interferons exhibit multiple biological activities such as antiviral, antiproliferative, immunomodulatory and anticellular functions. At least three distinct types of human interferons have been identified and characterized in terms of their biological activity such as antiviral, anti-growth and natural killer cell (NK) properties. They are produced by lymphocytes, diploid fibroblasts and the immune system and are classified as $\alpha$, $\beta$, and $\gamma$ interferons respectively. These are reported to be different proteins coded for by distinct structural genes.

The unavailability of adequate amounts of the pure material isolated from natural sources (native IFNs) and the expense involved, have precluded extensive clinical testing and evaluation of the extent of the therapeutic value of these interferons. Human interferons (HIFNs) are generally produced by superinducing appropriate human cell cultures with poly-IC (poly-riboinosinic acid and polyribocytidylic acid) and isolating and purifying the HIFN thus produced by chromatographic and electrophoretic techniques. However, interferon samples for use in clinical studies must be of relatively high purity and substantially uncontaminated with other proteins, antigens and extraneous toxic chemicals introduced during the extraction and purification steps. There are several methods currently available for the preparation, recovery and purification of IFNs.

Both affinity adsorption chromatography and high performance liquid chromatography have been separately used in the isolation and purification of proteins in general and of the various IFNs in particular.

Berg et al., Scand. J. Immunol., 8, 429–436 (1978) described the purification of human interferons by antibody affinity chromatography, using highly adsorbed antiinterferon as the ligand bound to the solid support matrix.

Berg, K., Scand. J. Immunol., 6, 77–86 (1977) taught a sequential affinity chromatographic technique for the purification of human leukocyte interferon.

Berg, K., et al., J. Immunol. 114, 640–644 (1975) also disclosed an affinity adsorption based chromatographic method for the isolation and purification of human $\alpha$ and $\beta$ IFNs using Sepharose-bound antibodies.

Okamura et al., Biochemistry, 19, 3831–3835 (1981) described the coupling of rabbit antiserum to cyanogen bromide activated Sepharose and using the resulting material for the purification of HIFN-$\beta$.

A major problem with the above methods of purification and recovery of IFN is that the protein is not produced in a pure enough form and in large enough yields or quantities for clinical, research and therapeutic purposes. Furthermore, the resulting IFN preparations have residual amounts of extraneous chemicals, such as sodium dodecyl sulfate (SDS) and other surfactants, extractants and/or percipitants, used in the extraction and purification steps. Thus some of these preparations may not be suitable or desirable for clinical studies designed to determine the extent of their therapeutic use and applications. Quite often, some of the extractants and surfactants used may denature the protein, and if not removed promptly, may eliminate a significant amount of the biological activity of the protein.

It would be desirable, therefore, to have available a process for the recovery of IFNs $\alpha$, $\beta$ and $\gamma$ in large enough quantities and without toxic levels of extraneous chemicals for clinical and therapeutic applications.

SUMMARY OF THE INVENTION

Accordingly, it is an object of the present invention to provide a pharmaceutically acceptable sample of $\alpha$, $\beta$ and $\gamma$ interferons which are of relatively high purity and which retain their full biological activity.

Another object of the present invention is to provide pharmaceutically acceptable samples of human interferons in sufficiently large quantities and yields for clinical, research and therapeutic applications.

Yet another object of the instant invention is to provide interferon preparations that are substantially free of ethanol, propanol, SDS and other chemicals used in the isolation process without loss of their biological activity, or present at levels that are therapeutically acceptable.

Additional objects, advantages and novel features of the invention will be set forth in part in the description which follows, and in part will become apparent to those skilled in the art upon examination of the following or may be learned by practice of the invention. The objects and advantages may be attained by means of the instrumentalities and combinations particularly pointed out in the appended claims.

To achieve the foregoing and other objects and in accordance with the purpose of the present invention, as embodied and broadly described herein, one aspect of the invention is an improved method for the isolation, recovery, and purification of IFNs and comprises initial purification of crude preparations of human IFNs by immunosorbent chromatography, followed by reverse phased high performance liquid chromatography (RP-HPLC) of the immunosorbent purified IFNs.

A preferred embodiment of the present invention comprises obtaining IFNs from appropriate cell sources by ammonium sulfate precipitation or similar methods known in the art, initially purifying the crude IFN preparations by anti-IFN-antibody affinity column chromatography or a similar, equivalent technique, cycling the immunosorbent purified IFN at least once, preferably twice, through an RP-HPLC column, eluting the IFN with a lower, aliphatic alcohol such as n-propanol over a linear gradient, extracting the alcohol with cyclohexane or other suitable solvents and removing the solvent by passing a stream of dry nitrogen through the IFN solution.

The HIFNs produced in accordance with the present invention are useful as therapeutic agents in viral infections, certain conditions of immunodeficiency, as antiproliferative agents and in other pathological conditions where HIFN therapy is indicated. They may also be used as standards for the determination of the specific activity of HIFNs produced by recombinant DNA techniques.

DETAILED DESCRIPTION OF THE INVENTION

Figure 1:
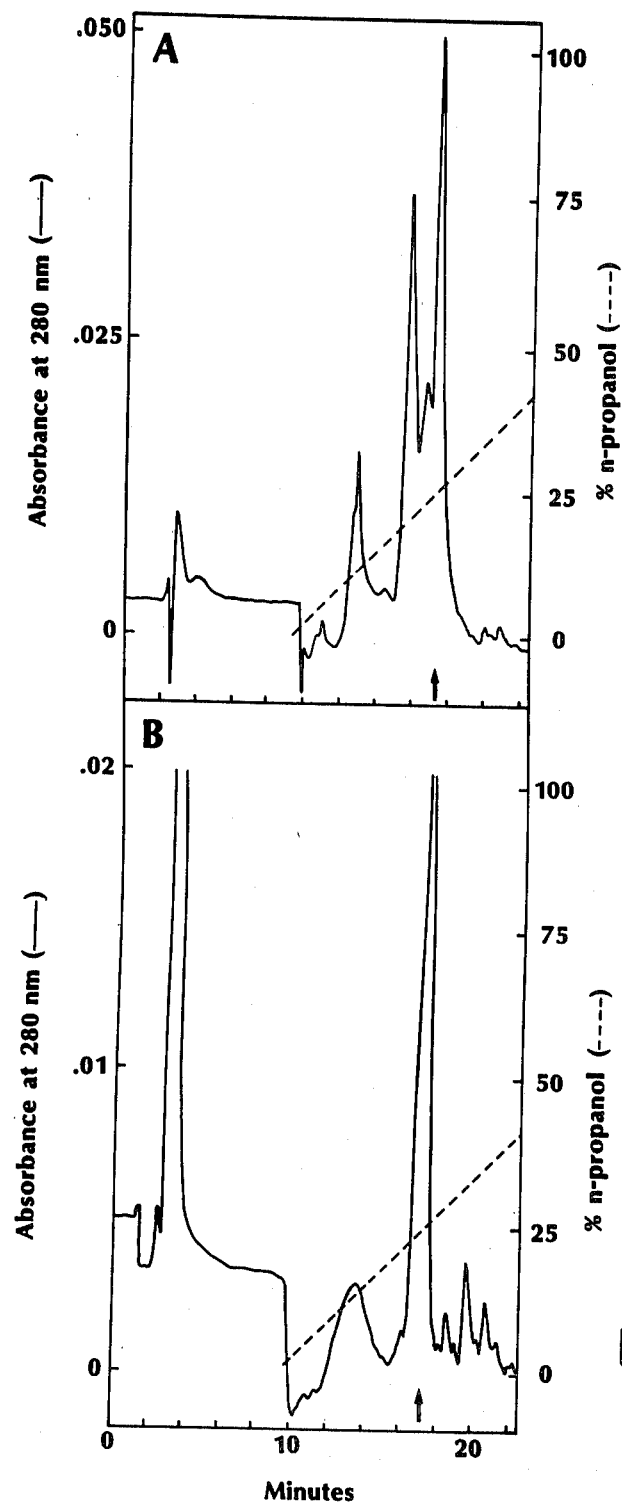
FIG. 1A shows the absorbance profile of immunosorbent-purified HIFN-$\beta$.
FIG. 1B represents an absorbance profile of RP-HPLC-purified HIFN-$\beta$.

The instant invention is a process for the isolation and purification of lipophilic proteins such as the interferons and comprises serially passing a partially purified solution of the proteins through an immunosorbent affinity column first and then through a reversed-phase high performance liquid chromatographic (RP-HPLC) column.

In a preferred embodiment, HIFN is initially obtained from appropriate human or other animal cells, and then superinduced for the production of HIFN by methods known in the art. (Tan et al. and Ho et al., infra). The HIFN purified by the process of the instant invention may be $\alpha$, $\beta$, or $\gamma$ and may be obtained from natural sources or may be produced by recombinant DNA techniques. The HIFN thus produced is concentrated and partially purified by ammonium sulfate precipitation or by molecular weight filtration using ultrafilters of appropriate molecular weight cut offs. Other known methods of protein precipitation, isolation and purification may also be employed. The ammonium sulfate precipitated protein is then resuspended in a suitable buffer such as phosphate or citrate buffer, in the pH range of about 7.0 to 7.5, and loaded on to an affinity adsorption chromatographic column. Typical affinity columns employ immunosorbent packing material such as antigens or antibodies immobilized on solid matrices. Preferred affinity columns are packed with antibodies attached to appropriate solid supports. Where HIFN is the protein, anti-HIFN antibodies, both polyclonal and monoclonal, immobilized on a suitable solid matrix can be employed. Materials suitable as the solid matrix support are known to those skilled in the art and are described in "An Introduction to Affinity Chromatography", C. R. Lowe, Laboratorty Techniques in Biochemistry and Molecular Biology, Eds. T. S. Work and E. Work, North-Holland Pub. Co., New York, 1979.

The adsorbed HIFN is then eluted from the affinity column with suitable solvents in an acidic pH range. Exemplary solvents are equilibrating buffers containing acetic acid, glycine-HCl and the like and suitable pH range from about 2.0 to about 3.0, preferably 2.2 to 2.9. The eluted HIFN is desalted (removal of ammonium sulfate) and concentrated by methods known in the art such as dialysis, ultrafiltration, diafiltration and the like.

The immunosorbent purified HIFN is then injected onto an RP-HPLC column packed with a suitable packing material. Typical packing materials are Lichrosorb, Silica, (consisting of silica particles) and the like. Immunosorbent-purified HIFN is then eluted over a linear gradient of an organic solvent with suitable eluotropic properties. Exemplary solvents are the lower aliphatic alcohols such as methanol, ethanol, n-propanol, 2-propanol, or may be other solvents such as acetic acid, dimethylformamide, acetone, acetonitrile, and dioxane. Preferred solvents are the lower aliphatic alcohols, n-propanol being the most preferred. Linear solvent gradients range from 0-100%. The eluate is, optionally, recycled through the HPLC column for better resolution and purification. Typically, two cycles through the RP-HPLC column yield homogeneous preparations with full biological activity.

The eluted HIFN may be subsequently concentrated by vacuum evaporation after removal of the organic solvent. When n-propanol is used as the organic solvent, it is removed by extraction with cyclohexane. The cyclohexane is then eliminated by passing a stream of dry nitrogen through the solution. Glycerol or a similar viscous, inert fluid may be added to the HIFN solution prior to vacuum concentration in order to reduce surface adsorption of the protein during vacuum concentration.

The instant invention yields HIFN in a substantially pure form, with full biological activity. It overcomes the problems of denaturation and loss of activity encountered in prior art methods where organic solvent extraction is utilized. By removing the n-propanol and cyclohexane prior to vacuum concentration, the biological activity of HIFN is retained.

The HIFN thus obtained, is assayed for protein concentration and for biological activity bY methods known to those skilled in the art. The HIFN purified by the present process is homogenous as measured by sodium dodecylsulfate-polyacrylamide gel electrophoresis (SDS-PAGE) and typically has a specific activity of about 4 to $5 \times 10^8$ IU/mg protein, with an overall yield in excess of 40%.

The following examples are presented only by way of illustration to describe the invention more fully and are not intended nor to be construed as limiting the invention to the specific modes described.

EXAMPLE 1

Cells and IFN Production

Normal human fibroblasts derived from foreskin explants were primed and then superinduced by the method of Tan et al., Proc. Nat'l. Acad. Sci., 67, 464 (1970) and of Ho et al., Proc. Soc. Exp. Biol. Med. 139, 259 (1972) and U.S. Pat. No. 3,773,924. The crude HIFN- was harvested in medium containing 1 mg/ml human serum albumin and concentrated by ammonium sulfate-precipitation.

EXAMPLE 2

Generation of Antibodies

Three BALB/c mice were each inoculated with 10–20 g of the purified interferon preparation weekly for 3 months. The purified antigen was mixed 1:1 v/v with Freund's adjuvant and injected intraperitoneally. One New Zealand White rabbit was inoculated with the same amount of antigen on a regimen similar to that for the mouse, except that in the first eight inoculations Freund's adjuvant was omitted and the routes of inoculation were by different routes such as intramuscular, intravenous, subcutaneous and the like. Test sera were obtained from the animals once weekly thereafter.

For determination of interferon neutralizing activity, an aliquot of the test serum diluted 100-fold was incubated with an equal volume of human interferon. After the incubation, the mixture was assayed for antiviral activity as described in Example 4 below. The neutralizing titer was obtained by first finding the well in which half the assay cells were protected; the value of the original interferon activity in that well was then multiplied by 200, the serum dilution factor. For example, if 50% protection occurred in a well containing $1 \times 10^3$ units of antiviral activity (prior to incubation), then the neutralizing titer of that serum would be $2 \times 10^5$ units/ml. Antiviral units were standardized as described above. (Okamura et al., Biochem., 19, 3831-35 (1980)). Antibodies may be polyclonal or monoclonal. Monoclonal antibodies were generated according to the method described by L. Nyari, et al., "Hybridoma" (1982) in press. The antibodies (polyclonal and monoclonal) were purified by the method of Inoue and Tan, infra (p. 11).

EXAMPLE 3

Preparation of Immunosorbent Column

The antibodies obtained in example 2 above were treated with 40% ammonium sulfate. The precipitated immunoglobulin fraction was sedimented by centrifugation at 1000 g for 15 min. It was further purified by HIFN affinity column or by other procedures known in the art. The precipitate was redissolved in 20 mM sodium phosphate buffer, pH 7.2, and dialyzed against the same buffer. The partially purified antiserum was then mixed with a slurry of cyanogen bromide activated Sepharose 4B (3 g dry weight, Pharmacia) in 0.1 M sodium bicarbonate, pH 8.3. The mixture was gently stirred overnight at 4° C., after which it was allowed to stand and the clear supernatant removed. This material was then treated with a 10-volume excess of 0.1 M Tris-HCl, pH 8.3, for 2 h. At the end of this treatment the Sepharose was washed with 0.1 M sodium borate buffer, pH 8.0 containing 1 M NaCl. This washing procedure was repeated 5 times. Thereafter, the Sepharose was washed in PB and stored at 4° C.

In a separate experiment, Sepharose CL4B was used as the column matrix. In this case it was activated with cyanogen bromide by a modified method of Cuatrecases & Anfinsen (Methods in Enzymol., 22, 345-351 (1971)) and immediately (within 60 s) mixed with the partially purified antiserum as described above.

EXAMPLE 4

Immunosorbent Chromatography

Ammonium sulfate-precipitated protein was resuspended in 20 mM sodium phosphate buffer, pH 7.2, containing 0.4M NaCl, 5% glycerol and 0.025 mM EDTA and loaded onto an anti-HIFN-$\beta$ affinity column as described by Okamura et al., Biochem, 19, 3831 (1980). The column was washed with 5 volumes 20 mM sodium acetate, pH 5.0 containing 50% ethylene glycol. The IFN was then eluted in 5 volumes 100 mM acetic acid, pH 2.9 followed by 5 volumes 100 mM glycine-HCl, pH 2.2. The IFN containing fractions were desalted and concentrated by Millipore CX-10 ultrafiltration (molecular weight cut-off 10,000). FIG. 1A shows the absorbance profile of the IFN obtained after immunosorbent affinity purification.

EXAMPLE 5

Reversed-phase HPLC

The HPLC system used consisted of a Waters model 720 system controller, model 440 absorbance detector, model 6000A solvent delivery system, M-45 solvent delivery system and model U6K universal liquid chromatograph injector. A Brownlee Aquapore-RP-300 analytical column (0.46 × 10 cm) equipped with a guard column (0.46 × 3 cm) was equilibrated with 100 mM formic acid, pH 2.44. All solvents used for HPLC were filtered and deaerated using a Millipore vacuum filtration system. Immunosorbent-purified IFN was injected onto the column and eluted with a 0-100% n-propanol linear gradient over 32 min at a flow rate of 0.6 ml/min. Under these conditions, IFN elutes about 17.5 min. after the beginning of the run corresponding to 23-25% n-propanol. The IFN containing fractions (0.5 min) were subjected to a second HPLC cycle using 200 mM formic acid, pH 2.38, as the aqueous phase. Fractions (0.5 min) were collected and stored at −20° C. FIG. 1B shows the homogeneity of the IFN obtained following HPLC purification. To allow subsequent vacuum concentration of the IFN without loss in activity, n-propanol was first removed by extraction with 4 volumes of cyclohexane. Residual cyclohexane was eliminated under a nitrogen stream. Glycerol (2 ul) was added to the remaining solution to reduce surface adsorption of IFN during the subsequent vacuum concentration.

EXAMPLE 6

Assay of HIFN-$\beta$

IFN was measured by a "sandwich" type radioimmunoassay utilizing rabbit antibodies directed against HIFN-$\beta$ as described by Inoue et al., Infect. Immune., 33, 763 (1981). In some cases, a biological assay was also performed. This assay is based on the method of Armstrong, App. Microbiol., 21, 723 (1971), using encephalomyocarditis virus and a HIFN-$\beta$ standard prepared in this laboratory against a HIFN-$\beta$ standard obtained from the N.I.H. (U.S.).

EXAMPLE 7

Measurement of Protein

Protein was determined by the method of Sedmak and Grossberg, Anal. Biochem., 79, 544 (1977), using bovine serum albumin (Sigma) and human serum albumin (Canadian Red Cross) as standards.

EXAMPLE 8

Polyacrylamide Gel Electrophoresis

Figure 2:
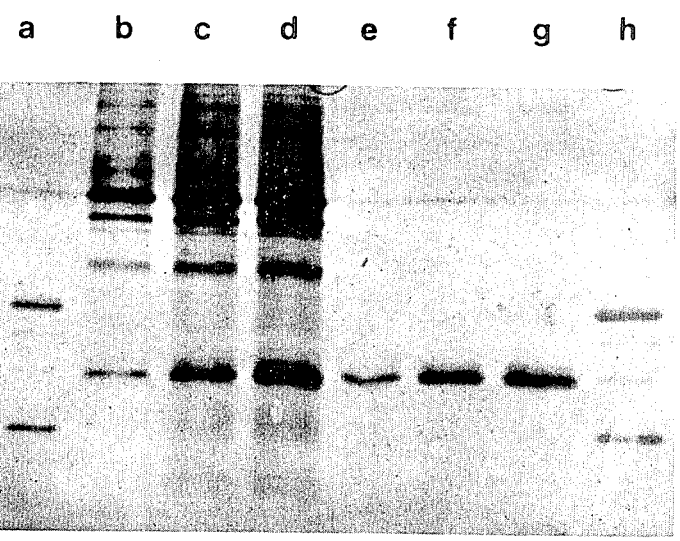
FIG. 2 shows the gel migration pattern of purified HIFN-$\beta$ using sodium dodecylsulfate-polyacrylamide gel electrophoretic (SDS-PAGE) analysis.

Slab SDS-PAGE was carried out according to Laemmli, Nature, 227, 680 (1970), using 0.75 mm-thick 12% acrylamide gels. Samples were prepared in 2 ul 0.0625 M Tris buffer, pH 6.8, containing 2% SDS, 5% $\beta$-mercaptoethanol and 100 mM thioglycolic acid and boiled for 3 min. prior to loading on the gel. Proteins were detected by silver staining according to Wray et al., Anal. Biochem., 118, with a sensitivity of at least 0.1 $\mu$g protein/band. FIG. 2 represents a gel migration pattern of HIFN purified by the present method and shows a homogeneous preparation of high purity.

The present invention thus provides a process whereby HIFN is obtained in better yields and which retains a high specific activity. The removal of n-propanol with cyclohexane prior to the concentration step is important for the retention of biological activity. The HIFN loses significant biological activity if it is left in contact with the eluting solvent n-propanol during or prior to the vacuum concentration step.

The HIFN obtained in accordance with the process of the instant invention may be lyophilized or stored in solution. Nontoxic, nontherapeutic, nonimmunogenic stabilizers may be optionally added to the HIFN. Diluents or carrier media that can be used in the solutions for therapeutic or clinical administrations are selected from aqueous based vehicles commonly used to formulate pharmaceuticals for animal or human administration. The diluent should, of course, not affect the biological activity of the HIFN. Examples of such diluents are distilled water, physiological saline, Ringer's solution, dextrose solution, Hank's solution and the like. The same diluents can be used to reconstitute lyophilized HIFN. The HIFNs isolated and purified by the process of this invention may be used for diagnostic, research and/or therapeutic applications where IFN therapy is indicated.

The foregoing description of the preferred emodiments of the instant invention have been presented for purposes of illustration and description. It is not intended to be exhaustive or to limit the invention to the precise form disclosed, and obviously many modifications and variations are possible in the light of the above teaching. The particular embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A process for the isolation and purification of a lipophilic interferon protein comprising
   (a) applying a solution of said protein to an immunosorbent adsorption affinity column;
   (b) eluting said protein from said affinity column with an equilibrating buffer;
   (c) passing the eluate from said affinity column containing said protein through a reversed-phase high performance liquid chromatographic column; and
   (d) eluting said protein from said chromatographic column with an organic solvent.

2. A process according to claim 1, wherein said equilibrating buffer is a plurality of buffers and said eluting is carried out serially with said plurality of buffers.

3. A process according to claim 1, wherein the pH of said equilibrating buffer is in the range of about 2.0 to about 3.0.

4. A process according to claim 1, wherein the organic solvent of step (d) is selected from the group consisting of methanol, ethanol, n-propanol, 2-propanol, dimethyl formamide, acetonitrile, acetone and dioxane.

5. A process according to claim 1, wherein said interferon is human interferon.

6. A process according to claim 5, wherein said human interferon is human fibroblast interferon.

7. A process according to claim 4, wherein said solvent is n-propanol.

8. A process according to claim 7, wherein said elution with n-propanol is used over a linear gradient.

9. A process according to claim 7 further comprising extracting said n-propanol with cyclohexane and removing said cyclohexane with a stream nitrogen.

10. A process for the isolation and purification of biologically active human interferon comprising:
    (a) applying a solution of ammonium sulfate precipitated HIFN to an antibody affinity column;
    (b) eluting said HIFN from said affinity column with a buffer;
    (c) ultrafiltering the eluate;
    (d) injecting said ultrafiltered HIFN solution onto a reverse-phase high performance liquid chromatographic column;
    (e) eluting said HIFN from said chromatographic column with a linear gradient flow of n-propanol;
    (f) extracting said n-propanol from the eluate with cyclohexane; and
    (g) remvoing residual cyclohexane from said HIFN solution with a stream of nitrogen.

11. A process for preparing human fibroblast interferon which process comprises
    (a) applying a solution at neutral pH of the human fibroblast interferon to an immunosorbent affinity column comprising antibodies to human fibroblast interferon immobilized on a solid support;
    (b) eluting the human fibroblast interferon with a buffer of pH about 2-3;
    (c) applying the human fibroblast interferon containing fractions from (b) to a reverse phase, high performance liquid chromatography column;
    (d) eluting the human fibroblast interferon from said chromatography column with a linear gradient flow of n-propanol.

12. The process of claim 11, which further includes extracting the n-propanol from the eluate with cyclohexane and removing residual cyclohexane with a stream of nitrogen.

* * * * *